(12) United States Patent
Conklin

(10) Patent No.: US 6,380,354 B1
(45) Date of Patent: Apr. 30, 2002

(54) KUNITZ DOMAIN POLYPEPTIDE ZKUN6

(75) Inventor: Darrell C. Conklin, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/388,183

(22) Filed: Sep. 1, 1999

Related U.S. Application Data

(60) Provisional application No. 60/099,296, filed on Sep. 3, 1998.

(51) Int. Cl.⁷ .................... A61K 38/00; C07K 2/00; C07K 4/00; C07K 5/00; C07K 7/00
(52) U.S. Cl. .................... 530/300; 530/324; 530/350
(58) Field of Search ................... 530/300, 350, 530/324

(56) References Cited

U.S. PATENT DOCUMENTS

| | | | |
|---|---|---|---|
| 5,780,265 A | 7/1998 | Dennis et al. | 435/69.2 |
| 5,795,865 A | 8/1998 | Markland et al. | 514/12 |
| 5,795,954 A | 8/1998 | Lazarus et al. | 530/324 |
| 5,834,244 A | 11/1998 | Dennis et al. | 435/69.2 |
| 5,880,256 A | 3/1999 | Dennis et al. | 530/324 |

FOREIGN PATENT DOCUMENTS

| WO | 95/18830 | 7/1995 |
|---|---|---|

OTHER PUBLICATIONS

Newlands and Skuce, GenBank Accession No. AF043121, 1998.
Percy, GenBank Accession No. Z84479, 1998.
INC1680228, LIFESEQ™ Information Results, Incyte Pharmaceuticals, Inc., 1998.
INC1678559, LIFESEQ™ Information Results, Incyte Pharmaceuticals, Inc., 1998.
Biotechnology Industry Organization, Critical Synergy: The Biotechnology Industry and Intellectual Property Protection, pp. 101, 103 and 104, 1993.*
Schwartz, G. et al. A superactive insulin: [B10–Aspartic acid]insulin (human), Proc. Natl. Acad. Sci. USA 84:6408–6411, 1987.*
Lin, Michael et al. Structure–Function Relationships in Glucagon: Properties of Highly Purified Des–His(1)–Monoiodo–, and Des–Asn(28), Thr(29)} (homoserine lactone, 27)–glucagon. Biochemistry 14(8): 1559–1563, 1975.*

\* cited by examiner

*Primary Examiner*—Anthony C. Caputa
*Assistant Examiner*—Alana M Harris
(74) *Attorney, Agent, or Firm*—Gary E. Parker

(57) ABSTRACT

Proteinase inhibitors comprising a Kunitz domain are disclosed. The Kunitz domain comprises a sequence of amino acid residues as shown in SEQ ID NO:3, wherein the sequence is at least 80% identical to residues 6 through 56 of SEQ ID NO:2. Also disclosed are methods for making the proteinase inhibitors, and expression vectors and cultured cells that are useful within the methods. The proteinase inhibitors may be used as components of cell culture media, in protein purification, and in certain therapeutic and diagnostic applications.

4 Claims, 1 Drawing Sheet

1KNT  : TDICKLPKDEGTCRDFILKWYYDPNTKSCARFWYGGCGGNENKFGSQKECEKVCA

ZKUN6 : GPGDACVLPAVQGPCRGWEPRWAYSPLLQQCHPFVYGGCEGNGNNFHSRESCEDACPVP

US 6,380,354 B1

KUNITZ DOMAIN POLYPEPTIDE ZKUN6

CROSS-REFERENCE TO RELATED APPLICATION

This application claims the benefit under 35 U.S.C. § 119(e) of Provisional Application No. 60/099,296, filed Sep. 3, 1998.

BACKGROUND OF THE INVENTION

In animals, proteinases are important in wound healing, extracellular matrix destruction, tissue reorganization, and in cascades leading to blood coagulation, fibrinolysis, and complement activation. Proteinases are released by inflammatory cells for destruction of pathogens or foreign materials, and by normal and cancerous cells as they move through their surroundings.

The activity of proteinases is regulated by inhibitors; 10% of the proteins in blood serum are proteinase inhibitors (Roberts et al., *Critical Reviews in Eukaryotic Gene Expression* 5:385–436, 1995). One family of proteinase inhibitors, the Kunitz inhibitors, includes inhibitors of trypsin, chymotrypsin, elastase, kallikrein, plasmin, coagulation factors XIa and IXa, and cathepsin G. These inhibitors thus regulate a variety of physiological processes, including blood coagulation, fibrinolysis, and inflammation.

Proteinase inhibitors regulate the proteolytic activity of target proteinases by occupying the active site and thereby preventing occupation by normal substrates. Although proteinase inhibitors fall into several unrelated structural classes, they all possess an exposed loop (variously termed an "inhibitor loop", a "reactive core", a "reactive site", or a "binding loop") which is stabilized by intermolecular interactions between residues flanking the binding loop and the protein core (Bode and Huber, *Eur. J. Biochem.* 204:433–451, 1992). Interaction between inhibitor and enzyme produces a stable complex which disassociates very slowly, releasing either virgin (uncleaved) inhibitor, or a modified inhibitor that is cleaved at the scissile bond of the binding loop.

One class of proteinase inhibitors, the Kunitz inhibitors, are generally basic, low molecular weight proteins comprising one or more inhibitory domains ("Kunitz domains"). The Kunitz domain is a folding domain of approximately 50–60 residues which forms a central anti-parallel beta sheet and a short C-terminal helix. This characteristic domain comprises six cysteine residues that form three disulfide bonds, resulting in a double-loop structure. Between the N-terminal region and the first beta strand resides the active inhibitory binding loop. This binding loop is disulfide bonded through the P2 Cys residue to the hairpin loop formed between the last two beta strands. Isolated Kunitz domains from a variety of proteinase inhibitors have been shown to have inhibitory activity (e.g., Petersen et al., *Eur. J. Biochem.* 125:310–316, 1996; Wagner et al., *Biochem. Biophys. Res. Comm.* 186:1138–1145, 1992; Dennis et al., *J. Biol. Chem.* 270:25411–25417, 1995).

Proteinase inhibitors comprising one or more Kunitz domains include tissue factor pathway inhibitor (TFPI), tissue factor pathway inhibitor 2 (TFPI-2), amyloid β-protein precursor (AβPP), aprotinin, and placental bikunin. TFPI, an extrinsic pathway inhibitor and a natural anticoagulant, contains three tandemly linked Kunitz inhibitor domains. The amino-terminal Kunitz domain inhibits factor VIIa, plasmin, and cathepsin G; the second domain inhibits factor Xa, trypsin, and chymotrypsin; and the third domain has no known activity (Petersen et al., ibid.). TFPI-2 has been shown to be an inhibitor of the amidolytic and proteolytic activities of human factor VIIa-tissue factor complex, factor XIa, plasma kallikrein, and plasmin (Sprecher et al., *Proc. Natl. Acad. Sci. USA* 91:3353–3357, 1994; Petersen et al., *Biochem.* 35:266–272, 1996). The ability of TFPI-2 to inhibit the factor VIIa-tissue factor complex and its relatively high levels of transcription in umbilical vein endothelial cells, placenta and liver suggests a specialized role for this protein in hemostasis (Sprecher et al., ibid.). Aprotinin (bovine pancreatic trypsin inhibitor) is a broad spectrum Kunitz-type serine proteinase inhibitor that has been shown to prevent activation of the clotting cascade. Aprotinin is a moderate inhibitor of plasma kallikrein and plamin, and blockage of fibrinolysis and extracorporeal coagulation have been detected in patients given aprotinin during open heart surgery (Davis and Whittington, *Drugs* 49:954–983, 1995; Dietrich et al., *Thorac. Cardiovasc. Surg.* 37:92–98, 1989). Aprotinin has also been used in the treatment of septic shock, adult respiratory distress syndrome, acute pancreatitis, hemorrhagic shock, and other conditions (Westaby, *Ann. Thorac. Surg.* 55:1033–1041, 1993; Wachtfogel et al., *J. Thorac. Cardiovasc. Surg.* 106:1–10, 1993). The clinical utility of aprotinin is believed to arise from its inhibitory activity towards plasma kallikrein or plasmin (Dennis et al., ibid.). Placental bikunin is a serine proteinase inhibitor containing two Kunitz domains (Delaria et al., *J. Biol. Chem.* 272:12209–12214, 1997). Individual Kunitz domains of bikunin have been expressed and shown to be potent inhibitors of trypsin, chymotrypsin, plasmin, factor XIa, and tissue and plasma kallikrein (Delaria et al., ibid.).

Known Kunitz-type inhibitors lack specificity and may have low potency. Lack of specificity can result in undesirable side effects, such as nephrotoxicity that occurs after repeated injections of high doses of aprotinin. These limitations may be overcome by preparing isolated Kunitz domains, which may have fewer side effects than traditional anticoagulants. Hence, there is a need in the art for additional Kunitz-type proteinase inhibitors.

SUMMARY OF THE INVENTION

It is an object of the present invention to provide novel Kunitz inhibitor proteins and compositions comprising the proteins. It is another object of the invention to provide materials and methods for making the Kunitz inhibitor proteins. It is a further object of the invention to provide antibodies that specifically bind to the Kunitz inhibitor proteins.

Within one aspect, the invention provides an isolated protein comprising a sequence of amino acid residues as shown in SEQ ID NO:3, wherein the sequence is at least 80% identical to residues 6 through 56 of SEQ ID NO:2. Within one embodiment, the protein is from 51 to 81 amino acid residues in length. Within another embodiment, the sequence is at least 90% identical to residues 6 through 56 of SEQ ID NO:2. Within another embodiment, the sequence consists of residues 6 through 56 of SEQ ID NO:2. Within other embodiments, the protein is from 51 to 67 residues in length, preferably from 55 to 62 residues in length. Within an additional embodiment, the protein further comprises an affinity tag. Suitable affinity tags include maltose binding protein, polyhistidine, and Glu-Tyr-Met-Pro-Met-Glu (SEQ ID NO:6).

Within a second aspect, the invention provides an expression vector comprising the following operably linked elements: (a) a transcription promoter; (b) a DNA segment encoding a protein as disclosed above; and (c) a transcription terminator. Within one embodiment, the expression vector further comprises a secretory signal sequence operably linked to the DNA segment.

Within a third aspect, the invention provides a cultured cell containing an expression vector as disclosed above, wherein the cell expresses the DNA segment. Within certain embodiments of the invention the cell is a yeast cell or a mammalian cell.

Within a fourth aspect of the invention there is provided a method of making a protein comprising culturing a cell as disclosed above under conditions whereby the DNA segment is expressed, and recovering the protein encoded by the DNA segment.

Within a fifth aspect of the invention there is provided an antibody that specifically binds to a protein of from 51 to 81 amino acid residues comprising a sequence of amino acid residues as shown in SEQ ID NO:3, wherein the sequence is at least 80% identical to residues 6 through 56 of SEQ ID NO:2.

These and other aspects of the invention will become evident upon reference to the following detailed description and the attached drawing.

BRIEF DESCRIPTION OF THE DRAWING

The attached drawing shows an amino acid sequence alignment of a representative polypeptide of the present invention (SEQ ID NO:2), designated "ZKUN6", with the sequence of the Kunitz domain of human alpha 3 type VI collagen (SEQ ID NO:5), designated "1KNT".

DETAILED DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Glu-Tyr-Met-Pro-Met-Glu; SEQ ID NO:6) (Grussenmeyer et al., *Proc. Natl. Acad. Sci. USA* 82:7952–4, 1985), substance P, Flag™ peptide (Hopp et al., *Biotechnology* 6:1204–10, 1988), streptavidin binding peptide, or other antigenic epitope or binding domain. See, in general, Ford et al., *Protein Expression and Purification* 2: 95–107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

A "complement" of a polynucleotide molecule is a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

A "DNA segment" is a portion of a larger DNA molecule having specified attributes. For example, a DNA segment encoding a specified polypeptide is a portion of a longer DNA molecule, such as a plasmid or plasmid fragment, that, when read from the 5' to the 3' direction, encodes the sequence of amino acids of the specified polypeptide.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774–78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as diners or alternatively glycosylated or derivatized forms.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When these terms are applied to double-stranded molecules they are used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired. Such unpaired ends will in general not exceed 20 nt in length.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an MRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention provides, in part, novel serine proteinases comprising a Kunitz domain. This Kunitz domain, including sequence variants thereof and proteins containing it, is referred to herein as "zkun6". The zkun6 polypeptide sequence shown in SEQ ID NO:2 comprises this Kunitz domain, which is bounded at the amino and carboxyl termini by cysteine residues at positions 6 and 56, respectively.

Zkun6 has 45% residue identity with the 51-residue kunitz domain in human alpha 3 type VI collagen (shown in SEQ ID NO:5). The structure of the latter domain has been solved by X-ray crystallography and by NMR (Arnoux et al., *J. Mol. Biol.* 246:609–617, 1995; Sorensen et al., *Biochemistry* 36:10439–10450, 1997). An alignment of zkun6 and the collagen Kunitz domain (see the drawing) can be combined with a homology model of zkun6 based on the X-ray structure to predict the function of certain residues in zkun6. Referring to SEQ ID NO:2, disulfide bonds are predicted to be formed by paired cysteine residues Cys6-Cys56; Cys15-Cys39; and Cys31-Cys52. The protease binding loop (P3–P4') is expected to comprise residues 14–20 of SEQ ID NO:2 (Pro-Cys-Arg-Gly-Trp-Glu-Pro), with the P1 residue being Arg16, and the P1' residue being Gly17.

Amino acid substitions can be made within the zkun6 sequence so long as the conserved cysteine residues are retained and the higher order structure is not disrupted. It is preferred to make substitutions within the zkun6 Kunitz domain by reference to the sequences of other Kunitz domains. SEQ ID NO:3 is a generalized Kunitz domain sequence that shows allowable amino acid substitutions based on such an alignment. The 51-residue sequence shown in SEQ ID NO:3 conforms to the pattern:

C-X(8)-C-X(15)-C-X(7)-C-X(12)-C-X(3)-C wherein C denotes cysteine; X is any naturally occuring amino acid residue, subject to the limitations set forth in the attached Sequence Listing for SEQ ID NO:3; and the numerals indicate the number of such variable residues. The second cysteine residue is in the P2 position.

Within the present invention up to 20% of the amino acid residues in the zkun6 Kunitz domain (residues 6 through 56 of SEQ ID NO:2) can be replaced with other amino acid residues, subject to the limitation that the resulting substituted sequence is one of the sequences disclosed in SEQ ID NO:3. The present invention thus provides a family of proteins comprising a sequence of amino acid residues as shown in SEQ ID NO:3, wherein the sequence is at least 80% identical to residues 6 through 56 of SEQ ID NO:2. It is preferred that the proteins of the present invention comprise such a sequence that is at least 85%, more preferably at least 90%, and most preferably at least 95% identical to residues 6 through 56 of SEQ ID NO:2.

Percent sequence identity is determined by conventional methods. See, for example, Altschul et al., *Bull. Math. Bio.* 48:603–616, 1986, and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 1 (amino acids are indicated by the standard one-letter codes). The percent identity is then calculated as:

Total number of identical matches/×100

[length of the longer sequence plus the number of gaps introduced into the longer sequence in order to align the two sequences]

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The level of identity between amino acid sequences can be determined using the "FASTA" similarity search algorithm disclosed by Pearson and Lipman (*Proc. Natl. Acad. Sci. USA* 85:2444, 1988) and by Pearson (*Meth. Enzymol.* 183:63, 1990). Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444, 1970; Sellers, *SIAM J. Appl. Math.* 26:787, 1974), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by modifying the scoring matrix file ("SMATRIX"), as explained in Appendix 2 of Pearson, 1990 (ibid.).

FASTA can also be used to determine the sequence identity of nucleic acid molecules using a ratio as disclosed above. For nucleotide sequence comparisons, the ktup value can range between one to six, preferably from three to six, most preferably three, with other parameters set as default.

The proteins of the present invention can also comprise non-naturally occurring amino acid residues. Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is carried out in a cell-free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Methods Enzymol.* 202:301, 1991; Chung et al., *Science* 259:806–9, 1993; and Chung et al., *Proc. Natl. Acad. Sci. USA* 90:10145–9, 1993). In a second method, translation is carried out in *Xenopus* oocytes by microinjection of mutated mRNA and chemically aminoacylated suppressor tRNAs (Turcatti et al., *J. Biol. Chem.* 271:19991–8, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–6, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993).

Additional polypeptides may be joined to the amino and/or carboxyl termini of the zkun6 Kunitz domain (residues 6–56 of SEQ ID NO:2) or a derivative of the zkun6 Kunitz domain as disclosed above. Particularly preferred proteins in this regard include residues 1–59 of SEQ ID NO:2. Amino and carboxyl extensions of the zkun6 Kunitz domain will be selected so as not to destroy or mask the proteinase-inhibiting activity of the protein by, for example, burying the Kunitz domain within the interior of the protein. There is a consequent preference for shorter extensions, typically 10–15 residues in length, preferably not exceeding 8 residues in length. There is considerable latitude in the permissible sequence of these extensions, although it is preferred to avoid the addition of cysteine residues in close proximity to the the Kunitz domain itself. For example, a zkun6 protein can comprise residues 6–56 of SEQ ID NO:2 with amino- and carboxyl-terminal dipeptides, wherein the individual amino acid residues of the dipeptides are any amino acid residue except cysteine.

Other amino- and carboxyl-terminal extensions that can be included in the proteins of the present invention include, for example, an amino-terminal methionine residue, a small linker peptide of up to about 20–25 residues, or an affinity tag as disclosed above. A protein comprising such an extension may further comprise a polypeptide linker and/or a proteolytic cleavage site between the zkun6 portion and the affinity tag. Preferred cleavage sites include thrombin cleavage sites and factor Xa cleavage sites. For example, a zkun6 polypeptide of 59 amino acid residues can be expressed as a fusion comprising, from amino terminus to carboxyl terminus: maltose binding protein (approximately 370 residues)—polyhistidine (6 residues)—thrombin cleavage site (Leu-Val-Pro-Arg; SEQ ID NO:7)—zkun6, resulting in a polypeptide of approximately 439 residues. In a second example, a zkun6 polypeptide of 81 residues can be fused to *E. coli* β-galactosidase (1,021 residues; see Casadaban et al., *J. Bacteriol.* 143:971–980, 1980), a 10-residue spacer, and a 4-residue factor Xa cleavage site to yield a polypeptide of 1,116 residues. Linker peptides and affinity tags provide for additional functions, such as binding to substrates, antibodies, binding proteins, and the like, and facilitate purification, detection, and delivery of zkun6 proteins. In another example, a zkun6 Kunitz domain can be expressed as a secreted protein comprising a carboxyl-terminal receptor transmembrane domain, permitting the Kunitz domain to be displayed on the surface of a cell. To span the lipid bilayer of the cell membrane, a minimum of about 20 amino acids are required in the transmembrane domain; these should predominantly be hydrophobic amino acids. The Kunitz domain can be separated from the transmembrane domain by a spacer polypeptide, and can be contained within an extended polypeptide comprising a carboxyl-terminal transmembrane domain—spacer polypeptide—Kunitz domain—amino-terminal polypeptide. Many receptor transmembrane domains and polynucleotides encoding them are known in the art. The spacer polypeptide will generally be at least about 50 amino acid residues in length, up to 200–300 or more residues. The amino terminal polypeptide may be up to 300 or more residues in length.

Also disclosed herein are polynucleotide molecules, including DNA and RNA molecules, encoding zkun6 proteins. These polynucleotides include the sense strand; the anti-sense strand; and the DNA as double-stranded, having both the sense and anti-sense strand annealed together by their respective hydrogen bonds. A representative DNA sequence encoding a zkun6 protein is set forth in SEQ ID NO:1. DNA sequences encoding other zkun6 proteins can be readily generated by those of ordinary skill in the art based on the genetic code. Counterpart RNA sequences can be generated by substitution of U for T. Polynucleotides encoding zkun6 proteins and complementary polynucleotides are useful in the production of zkun6 proteins and for diagnostic and investigatory purposes.

Those skilled in the art will readily recognize that, in view of the degeneracy of the genetic code, considerable sequence variation is possible among these polynucleotide molecules. SEQ ID NO:4 is a degenerate DNA sequence that encompasses all DNAs that encode the zkun6 polypeptide of SEQ ID NO:2. Those skilled in the art will recognize that the degenerate sequence of SEQ ID NO:4 also provides all RNA sequences encoding SEQ ID NO:2 by substituting U for T. Thus, zkun6 polypeptide-encoding polynucleotides comprising nucleotide 1 to nucleotide 177 of SEQ ID NO:4 and their respective RNA equivalents are contemplated by the present invention. Table 2 sets forth the one-letter codes used within SEQ ID NO:4 to denote degenerate nucleotide positions. "Resolutions" are the nucleotides denoted by a code letter. "Complement" indicates the code for the complementary nucleotide(s). For example, the code Y denotes either C or T, and its complement R denotes A or G, A being complementary to T, and G being complementary to C.

TABLE 2

| Nucleotide | Resolution | Nucleotide | Complement |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:4, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGI | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | . | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequences shown in SEQ ID NO:2. Variant sequences can be readily tested for functionality as described herein.

One of ordinary skill in the art will also appreciate that different species can exhibit preferential codon usage. See, in general, Grantham et al., *Nuc. Acids Res.* 8:1893–912, 1980; Haas et al. *Curr. Biol.* 6:315–24, 1996; Wain-Hobson et al., *Gene* 13:355–64, 1981; Grosjean and Fiers, Gene 18:199–209, 1982; Holm, *Nuc. Acids Res.* 14:3075–87, 1986; and Ikemura, *J. Mol. Biol.* 158:573–97, 1982. "Preferential codon usage" is a term of art referring to the bias in codon usage within the genomes of certain species, whereby certain protein translation codons are more frequently used, thus favoring one or a few representatives of the possible codons encoding each amino acid (see Table 3). For example, the amino acid threonine (Thr) may be encoded by ACA, ACC, ACG, or ACT, but in mammalian cells ACC is the most commonly used codon. In other species, for example, insect cells, yeast, viruses or bacteria, different Thr codons may be preferred. Preferred codons for a particular species can be introduced into the polynucleotides of the present invention by a variety of methods known in the art. Introduction of preferred codon sequences into recombinant DNA can, for example, enhance production of the protein by making protein translation more efficient within a particular cell type or species. Therefore, the degenerate codon sequence disclosed in SEQ ID NO:4 serves as a template for optimizing expression of polynucleotides in various cell types and species commonly used in the art and disclosed herein. Sequences containing preferred codons can be tested and optimized for expression in various host cell species, and tested for functionality as disclosed herein.

It is preferred that zkun6 polynucleotides hybridize to similar sized regions of SEQ ID NO:1, or a sequence complementary thereto, under stringent conditions. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is up to about 0.03 M at pH 7 and the temperature is at least about 60° C.

As previously noted, zkun6-encoding polynucleotides include DNA and RNA. Methods for preparing DNA and RNA are well known in the art. In general, RNA is isolated from a tissue or cell that produces large amounts of zkun6 RNA. Such tissues and cells are identified by conventional procedures, such as Northern blotting (Thomas, *Proc. Natl. Acad. Sci. USA* 77:5201, 1980). Total RNA can be prepared using guanidine-HCl extraction followed by isolation by centrifugation in a CsCl gradient (Chirgwin et al., *Biochemistry* 18:52–94, 1979). Poly (A)⁺ RNA is prepared from total RNA using the method of Aviv and Leder (*Proc. Natl. Acad. Sci. USA* 69:1408–12, 1972). Complementary DNA (cDNA) is prepared from poly(A)⁺ RNA using known methods. In the alternative, genomic DNA can be isolated. Polynucleotides encoding zkun6 polypeptides are then identified and isolated by, for example, hybridization or PCR.

A full-length clone encoding zkun6 can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zkun6, receptor fragments, or other specific binding partners.

The polynucleotides of the present invention can also be synthesized using automated equipment ("gene machines"). The current method of choice is the phosphoramidite method. If chemically synthesized double stranded DNA is required for an application such as the synthesis of a gene or a gene fragment, then each complementary strand is made separately. The production of short genes (60 to 80 bp) is technically straightforward and can be accomplished by synthesizing the complementary strands and then annealing them. For the production of longer genes (>300 bp), however, special strategies must be invoked, because the coupling efficiency of each cycle during chemical DNA synthesis is seldom 100%. To overcome this problem, synthetic genes (double-stranded) are assembled in modular form from single-stranded fragments that are from 20 to 100 nucleotides in length. Gene synthesis methods are well known in the art. See, for example, Glick and Pasternak, *Molecular Biotechnology, Principles & Applications of Recombinant DNA*, ASM Press, Washington, D.C., 1994; Itakura et al., *Annu. Rev. Biochem.* 53: 323–356, 1984; and Climie et al., *Proc. Natl. Acad. Sci. USA* 87:633–637, 1990.

The zkun6 polynucleotide sequences disclosed herein can be used to isolate counterpart polynucleotides from other species (orthologs). These orthologous polynucleotides can be used, inter alia, to prepare the respective orthologous proteins. These other species include, but are not limited to mammalian, avian, amphibian, reptile, fish, insect and other vertebrate and invertebrate species. Of particular interest are zkun6 polynucleotides and polypeptides from other mammalian species, including murine, porcine, ovine, bovine, feline, equine, and other primate polypeptides. Orthologs of human zkun6 can be cloned using information and compositions provided by the present invention in combination with conventional cloning techniques. For example, a cDNA can be cloned using mRNA obtained from a tissue or cell type that expresses zkun6 as disclosed herein. Suitable sources of mRNA can be identified by probing Northern blots with probes designed from the sequences disclosed herein. A library is then prepared from mRNA of a positive tissue or cell line. A zkun6-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zkun6 sequence disclosed herein. Within an additional method, the cDNA library can be used to transform or transfect host cells, and expression of the cDNA of interest can be detected with an antibody to zkun6 polypeptide. Similar techniques can also be applied to the isolation of genomic clones.

Those skilled in the art will recognize that the sequence disclosed in SEQ ID NO:1 represents a single allele of human zkun6 and that natural variation, including allelic variation and alternative splicing, is expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the proteinase inhibiting activity of zkun6 are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

Zkun6 proteins, including variants of wild-type zkun6, are tested for activity in protease inhibition assays, a variety of which are known in the art. Preferred assays include those measuring inhibition of trypsin, chymotrypsin, plasmin, cathepsin G, and human leukocyte elastase. See, for example, Petersen et al., *Eur. J. Biochem.* 235:310–316, 1996. In a typical procedure, the inhibitory activity of a test compound is measured by incubating the test compound with the proteinase, then adding an appropriate substrate, typically a chromogenic peptide substrate. See, for example, Norris et al. (*Biol. Chem. Hoppe-Seyler* 371:37–35 42, 1990). Briefly, various concentrations of the inhibitor are incubated in the presence of trypsin, plasmin, and plasma kallikrein in a low-salt buffer at pH 7.4, 25° C. After 30 minutes, the residual enzymatic activity is measured by the addition of a chromogenic substrate (e.g., S2251 (D-Val-Leu-Lys-Nan) or S2302 (D-Pro-Phe-Arg-Nan), available from Kabi, Stockholm, Sweden) and a 30-minute incubation. Inhibition of enzyme activity is indicated by a decrease in absorbance at 405 nm or fluorescence Em at 460 nm. From the results, the apparent inhibition constant $K_i$ is calculated. The inhibition of coagulation factors (e.g., factor VIIa, factor Xa) can be measured using chromogenic substrates or in conventional coagulation assays (e.g., clotting time of normal human plasma; Dennis et al., ibid.).

Zkun6 proteins can be tested in animal models of disease, particularly tumor models, models of fibrinolysis, and models of imbalance of hemostasis. Suitable models are known in the art. For example, inhibition of tumor metastasis can be assessed in mice into which cancerous cells or tumor tissue have been introduced by implantation or injection (e.g., Brown, *Advan. Enzyme Regul.* 35:293–301, 1995; Conway et al., *Clin. Exp. Metastasis* 14:115–124, 1996). Effects on fibrinolysis can be measured in a rat model wherein the enzyme batroxobin and radiolabeled fibrinogen are administered to test animals. Inhibition of fibrinogen activation by a test compound is seen as a reduction in the circulating level of the label as compared to animals not receiving the test compound. See, Lenfors and Gustafsson, *Semin. Thromb. Hemost.* 22:335–342, 1996. Zkun6 proteins can be delivered to test animals by injection or infusion, or can be produced in vivo by way of, for example, viral or naked DNA delivery systems or transgenic expression.

Exemplary viral delivery systems include adenovirus, herpesvirus, vaccinia virus and adeno-associated virus (AAV). Adenovirus, a double-stranded DNA virus, is currently the best studied gene transfer vector for delivery of heterologous nucleic acid (for a review, see Becker et al., *Meth. Cell Biol.* 43:161–189, 1994; and Douglas and Curiel, *Science & Medicine* 4:44–53, 1997). The adenovirus system offers several advantages: adenovirus can (i) accommodate relatively large DNA inserts; (ii) be grown to high titer; (iii) infect a broad range of mammalian cell types; and (iv) be used with a large number of available vectors containing different promoters. Also, because adenoviruses are stable in the bloodstream, they can be administered by intravenous injection. By deleting portions of the adenovirus genome, larger inserts (up to 7 kb) of heterologous DNA can be accommodated. These inserts can be incorporated into the viral DNA by direct ligation or by homologous recombination with a co-transfected plasmid. In an exemplary system, the essential E1 gene is deleted from the viral vector, and the virus will not replicate unless the E1 gene is provided by the host cell (e.g., the human 293 cell line). When intravenously administered to intact animals, adenovirus primarily targets the liver. If the adenoviral delivery system has an E1 gene deletion, the virus cannot replicate in the host cells. However, the host's tissue (e.g., liver) will express and process (and, if a signal sequence is present, secrete) the heterologous protein. Secreted proteins will enter the circulation in the highly vascularized liver, and effects on the infected animal can be determined.

An alternative method of gene delivery comprises removing cells from the body and introducing a vector into the cells as a naked DNA plasmid. The transformed cells are then re-implanted in the body. Naked DNA vectors are introduced into host cells by methods known in the art, including transfection, electroporation, microinjection, transduction, cell fusion, DEAE dextran, calcium phosphate precipitation, use of a gene gun, or use of a DNA vector transporter. See, Wu et al., *J. Biol. Chem.* 263:14621–14624, 1988; Wu et al., *J. Biol. Chem.* 267:963–967, 1992; and Johnston and Tang, *Meth. Cell Biol.* 43:353–365, 1994.

Transgenic mice, engineered to express a zkun6 gene, and mice that exhibit a complete absence of zkun6 gene function, referred to as "knockout mice" (Snouwaert et al., *Science* 257:1083, 1992), can also be generated (Lowell et al., *Nature* 366:740–742, 1993). These mice are employed to study the zkun6 gene and the encoded protein in an in vivo system. Transgenic mice are particularly useful for investigating the role of zkun6 proteins in early development because they allow the identification of developmental abnormalities or blocks resulting from the over- or under-expression of a specific factor.

The zkun6 polypeptides of the present invention, including full-length polypeptides, biologically active fragments, and fusion polypeptides can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zkun6 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zkun6 polypeptide into the secretory pathway of a host cell, a secretory signal sequence (also known as a leader sequence, prepro sequence or pre sequence) is provided in the expression vector. The secretory signal sequence may be that of zkun6, or may be derived from another secreted protein (e.g., t-PA) or synthesized de novo. The secretory signal sequence is operably linked to the zkun6 DNA sequence, i.e., the two sequences are joined in the correct reading frame and positioned to direct the newly sythesized polypeptide into the secretory pathway of the host cell. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are suitable hosts for use within the present invention. Methods for introducing exogenous DNA into mammalian host cells include calcium phosphate-mediated transfection (Wigler et al., Cell 14:725, 1978; Corsaro and Pearson, Somatic Cell Genetics 7:603, 1981: Graham and Van der Eb, Virology 52:456, 1973), electroporation (Neumann et al., EMBO J. 1:841–845, 1982), DEAE-dextran mediated transfection (Ausubel et al., ibid.), and liposome-mediated transfection (Hawley-Nelson et al., Focus 15:73, 1993; Ciccarone et al., Focus 15:80, 1993). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59–72, 1977) and Chinese hamster ovary (e.g. CHO-K1; ATCC No. CCL 61) cell lines. Additional suitable cell lines are known in the art and available from public depositories such as the American Type Culture Collection, 10801 University Boulevard, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter. Expression vectors for use in mammalian cells include pZP-1 and pZP-9, which have been deposited with the American Type Culture Collection, 10801 University Boulevard, Manassas, Va. under accession numbers 98669 and 98668, respectively.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. The use of Agrobacterium rhizogenes as a vector for expressing genes in plant cells has been reviewed by Sinkar et al., J. Biosci. (Bangalore) 11:47–58, 1987. Insect cells can be infected with recombinant baculovirus vectors, which are commonly derived from Autographa californica multiple nuclear polyhedrosis virus (AcMNPV). DNA encoding the polypeptide of interest is inserted into the viral genome in place of the polyhedrin gene coding sequence by homologous recombination in cells infected with intact, wild-type AcMNPV and transfected with a transfer vector comprising the cloned gene operably linked to polyhedrin gene promoter, terminator, and flanking sequences. The resulting recombinant virus is used to infect host cells, typically a cell line derived from the fall armyworm, Spodoptera frugiperda. See, in general, Glick and Pasternak, Molecular Biotechnology: Principles and Applications of Recombinant DNA, ASM Press, Washington, D.C., 1994.

Fungal cells, including yeast cells, can also be used within the present invention. Yeast species of particular interest in this regard include Saccharomyces cerevisiae, Pichia pastoris, and Pichia methanolica. Methods for transforming S. cerevisiae cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in Saccharomyces cerevisiae is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including Hansenula polymorpha, Schizosaccharomyces pombe, Kluyveromyces lactis, Kluyveromyces fragilis, Ustilago maydis, Pichia pastoris, Pichia methanolica, Pichia guillermondii and Candida maltosa are known in the art. See, for example, Gleeson et al., J. Gen. Microbiol. 132:3459–3465, 1986 and Cregg, U.S. Pat. No. 4,882,279. Aspergillus cells may be utilized according to the methods of McKnight et al., U.S. Pat. No. 4,935,349. Methods for transforming Acremonium chrysogenum are disclosed by Sumino et al., U.S. Pat. No. 5,162,228. Methods for transforming Neurospora are disclosed by Lambowitz, U.S. Pat. No. 4,486,533. Production of recombinant proteins in Pichia methanolica is disclosed in U.S. Pat. Nos. 5,716,808, 5,736,383, 5,854,039, and 5,888,768.

Prokaryotic host cells, including strains of the bacteria Escherichia coli, Bacillus and other genera are also useful host cells within the present invention. Techniques for transforming these hosts and expressing foreign DNA sequences cloned therein are well known in the art (see, e.g., Sambrook et al., ibid.). When expressing a zkun6 polypeptide in bacteria such as E. coli, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors.

It is preferred to purify the proteins of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified protein is substantially free of other proteins, particularly other proteins of animal origin.

Zkun6 proteins are purified by conventional protein purification methods, typically by a combination of chromatographic techniques. Polypeptides comprising polyhistidine affinity tag (typically about 6 histidine residues) are purified by affinity chromatography on a nickel chelate resin. See, for example, Houchuli et al., *Bio/Technol.* 6: 1321–1325, 1988.

Using methods known in the art, zkun6 proteins can be produced glycosylated or non-glycosylated; pegylated or non-pegylated; and may or may not include an initial methionine amino acid residue.

The zkun6 proteins are contemplated for use in the treatment or prevention of conditions associated with excessive proteinase activity, in particular an excess of trypsin, plasmin, kallikrein, elastase, cathepsin G, proteinase-3, thrombin, factor VIIa, factor IXa, factor Xa, factor XIa, factor XIIa, or matrix metalloproteinases. Such conditions include, but are not limited to, acute pancreatitis, cardiopulmonary bypass (CPB)-induced pulmonary injury, allergy-induced protease release, deep vein thrombosis, myocardial infarction, shock (including septic shock), hyperfibrinolytic hemorrhage, emphysema, rheumatoid arthritis, adult respiratory distress syndrome, chronic inflammatory bowel disease, psoriasis, and other inflammatory conditions. Zkun6 proteins are also contemplated for use in preservation of platelet function, organ preservation, and wound healing.

Zkun6 proteins may be useful in the treatment of conditions arising from an imbalance in hemostasis, including acquired coagulopathies, primary fibrinolysis and fibrinolysis due to cirrhosis, and complications from high-dose thrombolytic therapy. Acquired coagulopathies can result from liver disease, uremia, acute disseminated intravascular coagulation, post-cardiopulmonary bypass, massive transfusion, or Warfarin overdose (Humphries, *Transfusion Medicine* 1:1181–1201, 1994). A deficiency or dysfunction in any of the procoagulant mechanisms predisposes the patient to either spontaneous hemorrhage or excess blood loss associated with trauma or surgery. Acquired coagulopathies usually involve a combination of deficiencies, such as deficiencies of a plurality of coagulation factors, and/or platelet dysfunction. In addition, patients with liver disease commonly experience increased fibrinolysis due to an inability to maintain normal levels of $\alpha_2$-antiplasmin and/or decreased hepatic clearance of plasminogen activators (Shuman, *Hemorrhagic Disorders*, in Bennet and Plum, eds. *Cecil Textbook of Medicine*, 20th ed, W.B. Saunders Co., 1996). Primary fibrinolysis results from a massive release of plasminogen activator. Conditions associated with primary fibrinolysis include carcinoma of the prostate, acute promyelocytic leukemia, hemangiomas, and sustained release of plasminogen activator by endothelial cells due to injection of venoms. The condition becomes critical when enough plasmin is activated to deplete the circulating level of $\alpha_2$-antiplasmin (Shuman, ibid.). Data suggest that plasmin on endothelial cells may be related to the pathophysiology of bleeding or rethrombosis observed in patients undergoing high-dose thrombolytic therapy for thrombosis. Plasmin may cause further damage to the thrombogenic surface of blood vessels after thrombolysis, which may result in rethrombosis (Okajima, *J. Lab. Clin. Med.* 126:1377–1384, 1995).

Additional antithrombotic uses of zkun6 proteins include treatment or prevention of deep vein thrombosis, pulmonary embolism, and post-surgical thrombosis.

Zkun6 proteins may also be used within methods for inhibiting blood coagulation in mammals, such as in the treatment of disseminated intravascular coagulation. Zkun6 proteins may thus be used in place of known anticoagulants such as heparin, coumarin, and anti-thrombin III. Such methods will generally include administration of the protein in an amount sufficient to produce a clinically significant inhibition of blood coagulation. Such amounts will vary with the nature of the condition to be treated, but can be predicted on the basis of known assays and experimental animal models, and will in general be within the ranges disclosed below.

Zkun6 proteins may also find therapeutic use in the blockage of proteolytic tissue degradation. Proteolysis of extracellular matrix, connective tissue, and other tissues and organs is an element of many diseases. This tissue destruction is believed to be initiated when plasmin activates one or more matrix metalloproteinases (e.g., collagenase and metallo-elastases). Inhibition of plasmin by zkun6 proteins may thus be beneficial in the treatment of these conditions.

Matrix metalloproteinases (MMPs) are believed to play a role in metastases of cancers, abdominal aortic aneurysm, multiple sclerosis, rheumatoid arthritis, osteoarthritis, trauma and hemorrhagic shock, and cornial ulcers. MMPs produced by tumor cells break down and remodel tissue matrices during the process of metastatic spread. There is evidence to suggest that MMP inhibitors may block this activity (Brown, *Advan. Enzyme Regul.* 35:293–301, 1995). Abdominal aortic aneurysm is characterized by the degradation of extracellular matrix and loss of structural integrity of the aortic wall. Data suggest that plasmin may be important in the sequence of events leading to this destruction of aortic matrix (Jean-Claude et al., *Surgery* 116:472–478, 1994). Proteolytic enzymes are also believed to contribute to the inflammatory tissue damage of multiple sclerosis (Gijbels, *J. Clin. Invest.* 94:2177–2182, 1994). Rheumatoid arthritis is a chronic, systemic inflammatory disease predominantly affecting joints and other connective tissues, wherein proliferating inflammatory tissue (panus) may cause joint deformities and dysfunction (see, Arnett, in *Cecil Textbook of Medicine*, ibid.). Osteoarthritis is a chronic disease causing deterioration of the joint cartilage and other joint tissues and the formation of new bone (bone spurs) at the margins of the joints. There is evidence that MMPs participate in the degradation of collagen in the matrix of osteoarthritic articular cartilage. Inhition of MMPs results in the inhibition of the removal of collagen from cartilage matrix (Spirito, *Inflam. Res.* 44 (supp. 2):S131–S132, 1995; O'Byrne, *Inflam. Res.* 44 (supp. 2):S117–S118, 1995; Karran, *Ann. Rheumatic Disease* 54:662–669, 1995). Zkun6 proteins may also be useful in the treatment of trauma and hemorrhagic shock. Data suggest that administration of an MmP inhibitor after hemorrhage improves cardiovascular response, hepatocellular function, and microvascular blood flow in various organs (Wang, *Shock* 6:377–382, 1996). Corneal ulcers, which can result in blindness, manifest as a breakdown of the collagenous stromal tissue. Damage due to thermal or chemical injury to corneal surfaces often results in a chronic wound-healing situation. There is direct evidence for the role of MMPs in basement membrane defects associated with failure to re-epithelialize in cornea or skin (Fini, *Am. J. Pathol.* 149:1287–1302, 1996).

The zkun6 proteins of the present invention may be combined with other therapeutic agents to augment the activity (e.g., antithrombotic or anticoagulant activity) of such agents. For example, a zkun6 protein may be used in combination with tissue plasminogen activator in thrombolytic therapy.

Doses of zkun6 proteins will vary according to the severity of the condition being treated and may range from approximately 10 µg/kg to 10 mg/kg body weight, preferably 100 µg/kg to 5 mg/kg, more preferably 100 µg/kg to 1 mg/kg. The proteins formulated in a pharmaceutically acceptable carrier or vehicle. It is preferred to prepare them in a form suitable for injection or infusion, such as by dilution with with sterile water, an isotonic saline or glucose solution, or similar vehicle. In the alternative, the protein may be packaged as a lyophilized powder, optionally in combination with a pre-measured diluent, and resuspended immediately prior to use. Pharmaceutical compositions may further include one or more excipients, preservatives, solubilizers, buffering agents, albumin to prevent protein loss on vial surfaces, etc. Formulation methods are within the level of ordinary skill in the art. See, *Remington: The Science and Practice of Pharmacy*, Gennaro, ed., Mack Publishing Co., Easton, Pa., 19th ed., 1995.

Gene therapy provides an alternative therapeutic approach for delivery of zkun6 proteins. If a mammal has a mutated or absent zkun6 gene, a polynucleotide encoding a zkun6 protein can be introduced into the cells of the mammal. In one embodiment, a gene encoding a zkun6 protein is introduced in vivo in a viral vector. Such vectors include an attenuated or defective DNA virus, such as herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, without limitation, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–8, 1989).

Within another embodiment, a zkun6 polynucleotide can be introduced in a retroviral vector, as described, for example, by Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; Dougherty et al., WIPO Publication No. WO 95/07358; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–7, 1987; Mackey et al., *Proc. Natl. Acad. Sci. USA* 85:8027–31, 1988).

Within a further embodiment, target cells are removed from the body, and a vector is introduced into the cells as a naked DNA plasmid. The transformed cells are then re-implanted into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, for example, Wu et al., *J. Biol. Chem.* 267:963–7, 1992; Wu et al., *J. Biol. Chem.* 263:14621–4, 1988.

Zkun6 proteins can also be used to prepare antibodies that specifically bind to zkun6 proteins. As used herein, the term "antibodies" includes polyclonal antibodies, monoclonal antibodies, antigen-binding fragments thereof such as F(ab')$_2$ and Fab fragments, single chain antibodies, and the like, including genetically engineered antibodies. Non-human antibodies can be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. One skilled in the art can generate humanized antibodies with specific and different constant domains (i.e., different Ig subclasses) to facilitate or inhibit various immune functions associated with particular antibody constant domains. Alternative techniques for generating or selecting antibodies useful herein include in vitro exposure of lymphocytes to a zkun6 protein, and selection of antibody display libraries in phage or similar vectors (for instance, through use of immobilized or labeled zkun6 polypeptide). Antibodies are defined to be specifically binding if they bind to a zkun6 protein with an affinity at least 10-fold greater than the binding affinity to control (non-zkun6) polypeptide. It is preferred that the antibodies exhibit a binding affinity ($K_a$) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The affinity of a monoclonal antibody can be readily determined by one of ordinary skill in the art (see, for example, Scatchard, *Ann. NY Acad. Sci.* 51: 660–672, 1949).

Methods for preparing polyclonal and monoclonal antibodies are well known in the art (see for example, Hurrell, J. G. R., Ed., *Monoclonal Hybridoma Antibodies: Techniques and Applications*, CRC Press, Inc., Boca Raton, Fla., 1982). As would be evident to one of ordinary skill in the art, polyclonal antibodies can be generated from a variety of warm-blooded animals such as horses, cows, goats, sheep, dogs, chickens, rabbits, mice, and rats. The immunogenicity of a zkun6 protein may be increased through the use of an adjuvant such as alum (aluminum hydroxide) or Freund's complete or incomplete adjuvant. Polypeptides useful for immunization also include fusion polypeptides, such as fusions of a zkun6 protein or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

Immunogenic zkun6 polypeptides may be as small as 5 residues. It is preferred to use polypeptides that are hydrophilic or comprise a hydrophilic region. A preferred such region of SEQ ID NO:2 includes residues 44 (Asn)–54 (Asp).

A variety of assays known to those skilled in the art can be utilized to detect antibodies that specifically bind to a zkun6 protein. Exemplary assays are described in detail in *Antibodies: A Laboratory Manual*, Harlow and Lane (Eds.), Cold Spring Harbor Laboratory Press, 1988. Representative examples of such assays include concurrent immunoelectrophoresis, radio-immunoassays, radio-immunoprecipitations, enzyme-linked immunosorbent assays (ELISA), dot blot assays, Western blot assays, inhibition or competition assays, and sandwich assays.

Antibodies to zkun6 may be used for affinity purification of zkun6 proteins; within diagnostic assays for determining circulating levels of zkun6 proteins; for detecting or quantitating soluble zkun6 protein as a marker of underlying pathology or disease; for immunolocalization within whole animals or tissue sections, including immunodiagnostic applications; for immunohistochemistry; for screening expression libraries; and for other uses that will be evident to those skilled in the art. For certain applications, including in vitro and in vivo diagnostic uses, it is advantageous to employ labeled antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates.

Zkun6 proteins may be used in the laboratory or commercial preparation of proteins from cultured cells. The proteins can be used alone to inhibit specific proteolysis or can be combined with other proteinase inhibitors to provide a "cocktail" with a broad spectrum of activity. Of particular interest is the inhibition of cellular proteases, which can be release during cell lysis. The proteins can also be used in the laboratory as a tissue culture additive to prevent cell detachment.

The invention is further illustrated by the following non-limiting example.

EXAMPLE

To obtain a Zkun6 cDNA clone, cDNA is prepared from stomach using a a commercially available kit (Marathon™ cDNA Amplification Kit from Clontech Laboratories, Inc., Palo Alto, Calif.) and an oligo(dT) primer. To amplify the zkun6 DNA, 5 µl each of 1/100 diluted cDNAs, 20 pmoles each of two oligonucleotide primers designed from SEQ ID NO:1, and 1 U of a 2:1 mixture of ExTaq™ DNA polymerase (TaKaRa Biomedicals) and Pfu DNA polymerasse (Stratagene, La Jolla, Calif.) (ExTaq/Pfu) are used in a 25-µl reaction mixture. The reaction mixture is incubated at 94° C. for 2 minutes; 25 cycles of 94° C. for 15 seconds, 66° C. for 20 seconds, and 72° C. for 30 seconds; and a 1-minute incubation at 72° C. 1 µl each of 1/100 diluted first PCR product is used as template for a nested PCR. 20 pmoles each of two additional oligonucleotide primers and 1 U of ExTaq/Pfu are used in 25-µl reaction mixtures. The mixtures are incubated at 94° C. for 2 minutes; 2 cycles of 94° C. for 15 seconds, 66° C. for 20 seconds, 72° C. for 30 seconds; 25 cycles of 94° C. for 15 seconds, 64° C. for 20 seconds, 72° C. for 30 seconds; and a 1-minute incubation at 72° C. The PCR products are gel purified and sequenced to confirm their identity.

To construct an expression vector for the zkun6 Kunitz domain, PCR is performed on cDNA prepared from stomach as disclosed above. Primers are designed such that the PCR product will encode an intact Kunitz domain with restriction sites Bam HI in the sense primer and Xho I in the antisense primer to facilitate subdloning into an expression vector. 5 µl of 1/100 diluted cDNA, 20 pmoles of each oligonucleotide primer, and 1 U of ExTaq/Ffu are used in 25-µl reaction mixtures. The mixtures are incubated at 94° C. for 2 minutes; 3 cycles of 94° C. for 30 seconds, 50° C. for 30 seconds, 72° C. for 30 seconds; 35 cycles of 94° C. for 30 seconds, 68° C. for 30 seconds; and a 7-minute incubation at 72° C. The PCR product is gel purified and restriction digested with Bam HI and Xho I overnight.

A mammalian expression vector was constructed with the dihyrofolate reductase gene selectable marker under control of the SV40 early promoter, SV40 polyadenylation site, a cloning site to insert the gene of interest under control of the mouse metallothionein 1 (MT-1) promoter and the hGH polyadenylation site. The expression vector was designated pZP-9 and has beer, deposited at the American Type Culture Collection, 10801 University Boulevard, Manassas, Va. under accession no 98668. To facilitate protein purification, the pZP9 vector was modified by addition of a tissue plasminogen activator (t-PA) secretory signal sequence (see U.S. Pat. No. 5,641,655) and a GluGlu tag sequence (SEQ ID NQ:6) between the MT-1 promoter and hGH terminator. The t-PA secretory signal sequence replaces the native secretory signal sequence for DNAs encoding polypeptides of interest that are inserted into this vector, and expression results in an N-terminally tagged protein. The N-terminally tagged vector was designated pZP9NEE. The vector PZP-NEE is digested with Bam HI and Xho I, and the zkun6 fragment is inserted. The resulting construct is confirmed by sequencing.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

I claim:

1. An isolated protein comprising a sequence of amino acid residues as shown in SEQ ID NO:2 from residue 6 through residue 56, wherein said protein is at least 51 amino acid residues in length and not more than 81 amino acid residues in length.

2. The isolated protein of claim 1 wherein said protein is not more than 59 amino acid residues in length.

3. The isolated protein of claim 1 which consists of residues 6 through 56 of SEQ ID NO:2.

4. The isolated protein of claim 1 which consists of residues 1 through 59 of SEQ ID NO:2.

* * * * *

SEQUENCE LISTING

<160> NUMBER OF SEQ ID NOS: 7

<210> SEQ ID NO 1
<211> LENGTH: 177
<212> TYPE: DNA
<213> ORGANISM: Homo sapiens
<220> FEATURE:
<221> NAME/KEY: CDS
<222> LOCATION: (1)...(177)

<400> SEQUENCE: 1

```
ggc ccc ggc gac gcc tgc gtg ctg cct gcc gtg cag ggc ccc tgc cgg      48
Gly Pro Gly Asp Ala Cys Val Leu Pro Ala Val Gln Gly Pro Cys Arg
 1               5                  10                  15 ggc tgg gag ccg cgc tgg gcc tac agc ccg ctg ctg cag cag tgc cat      96
Gly Trp Glu Pro Arg Trp Ala Tyr Ser Pro Leu Leu Gln Gln Cys His
             20                  25                  30 ccc ttc gtg tac ggt ggc tgc gag ggc aac ggc aac aac ttc cac agc     144
Pro Phe Val Tyr Gly Gly Cys Glu Gly Asn Gly Asn Asn Phe His Ser
         35                  40                  45 cgc gag agc tgc gag gat gcc tgc ccc gtg ccg                         177
Arg Glu Ser Cys Glu Asp Ala Cys Pro Val Pro
     50                  55
```

<210> SEQ ID NO 2
<211> LENGTH: 59
<212> TYPE: PRT
<213> ORGANISM: Homo sapiens

<400> SEQUENCE: 2

```
Gly Pro Gly Asp Ala Cys Val Leu Pro Ala Val Gln Gly Pro Cys Arg
 1               5                  10                  15

Gly Trp Glu Pro Arg Trp Ala Tyr Ser Pro Leu Leu Gln Gln Cys His
             20                  25                  30

Pro Phe Val Tyr Gly Gly Cys Glu Gly Asn Gly Asn Asn Phe His Ser
         35                  40                  45

Arg Glu Ser Cys Glu Asp Ala Cys Pro Val Pro
     50                  55
```

<210> SEQ ID NO 3
<211> LENGTH: 51
<212> TYPE: PRT
<213> ORGANISM: Artificial Sequence
<220> FEATURE:
<223> OTHER INFORMATION: Kunitz motif
<220> FEATURE:
<221> NAME/KEY: VARIANT
<222> LOCATION: (2)...(2)
<223> OTHER INFORMATION: Xaa is any residue except Asp, Cys, Gly,
      His, Met, Pro or Trp
<220> FEATURE:
<221> NAME/KEY: VARIANT
<222> LOCATION: (3)...(3)
<223> OTHER INFORMATION: Xaa is Leu, Glu, Met, Gln, Phe, Ser, Thr,
      Ala or Pro
<220> FEATURE:
<221> NAME/KEY: VARIANT
<222> LOCATION: (4)...(4)
<223> OTHER INFORMATION: Xaa is any residue except Arg, Cys, Met,
      Phe, Trp, Tyr or Val
<220> FEATURE:
<221> NAME/KEY: VARIANT
<222> LOCATION: (5)...(5)
<223> OTHER INFORMATION: Xaa is any residue except Asn, Cys, Gln,
      Gly, Phe, Ser, Thr or Trp
<220> FEATURE:

```
<221> NAME/KEY: VARIANT
<222> LOCATION: (6)...(6)
<223> OTHER INFORMATION: Xaa is Arg, Glu, Asn, Ala, Val, Asp, Lys,
      Ser, Tyr or Met
<220> FEATURE:
<221> NAME/KEY: VARIANT
<222> LOCATION: (7)...(7)
<223> OTHER INFORMATION: Xaa is any residue except Asn, Cys, Gly,
      His, Leu, Met, Phe or Trp
<220> FEATURE:
<221> NAME/KEY: VARIANT
<222> LOCATION: (8)...(8)
<223> OTHER INFORMATION: Xaa is Gly or Glu
<220> FEATURE:
<221> NAME/KEY: VARIANT
<222> LOCATION: (9)...(9)
<223> OTHER INFORMATION: Xaa is Pro, Arg, Leu, Val, Ser, Asp, Ile,
      Asn or Thr
<220> FEATURE:
<221> NAME/KEY: VARIANT
<222> LOCATION: (11)...(11)
<223> OTHER INFORMATION: Xaa is any residue except Ala, Cys, Glu,
      His, Ile, Pro, Trp or Val
<220> FEATURE:
<221> NAME/KEY: VARIANT
<222> LOCATION: (12)...(12)
<223> OTHER INFORMATION: Xaa is Arg, Lys, Ala, Asp, Gln, Phe, Gly,
      Glu, Thr or Ser
<220> FEATURE:
<221> NAME/KEY: VARIANT
<222> LOCATION: (13)...(13)
<223> OTHER INFORMATION: Xaa is any residue except Asp, Cys, Glu,
      Pro or Thr
<220> FEATURE:
<221> NAME/KEY: VARIANT
<222> LOCATION: (14)...(14)
<223> OTHER INFORMATION: Xaa is any residue except Arg, Asn, Cys, Gly,
      His, Ser,
<223>  Trp or Tyr
<220> FEATURE:
<221> NAME/KEY: VARIANT
<222> LOCATION: (15)...(15)
<223> OTHER INFORMATION: Xaa is any residue except Ala, Asp, Cys, Gly,
      His, Met,
<223> Trp or Tyr
<220> FEATURE:
<221> NAME/KEY: VARIANT
<222> LOCATION: (16)...(16)
<223> OTHER INFORMATION: Xaa is Ser, Ala, Arg, Val, Gln, Lys, Leu,
      Gly or Ile
<220> FEATURE:
<221> NAME/KEY: VARIANT
<222> LOCATION: (17)...(17)
<223> OTHER INFORMATION: Xaa is Phe, Tyr, Ile, Trp or Leu
<220> FEATURE:
<221> NAME/KEY: VARIANT
<222> LOCATION: (18)...(18)
<223> OTHER INFORMATION: Xaa is Tyr, His, Phe, Trp, Asn or Ala
<220> FEATURE:
<221> NAME/KEY: VARIANT
<222> LOCATION: (19)...(19)
<223> OTHER INFORMATION: Xaa is Tyr or Phe
<220> FEATURE:
<221> NAME/KEY: VARIANT
<222> LOCATION: (20)...(20)
<223> OTHER INFORMATION: Xaa is Lys, Asn, Ser or Asp
<220> FEATURE:
<221> NAME/KEY: VARIANT
<222> LOCATION: (21)...(21)
<223> OTHER INFORMATION: Xaa is any residue except Asp, Cys, Glu,
      His or Tyr
<220> FEATURE:
<221> NAME/KEY: VARIANT
<222> LOCATION: (22)...(22)
<223> OTHER INFORMATION: Xaa is any residue except Cys, Met, Pro or Trp
<220> FEATURE:
<221> NAME/KEY: VARIANT
<222> LOCATION: (23)...(23)
<223> OTHER INFORMATION: Xaa is Ala, Lys, Ser, Leu, Thr, Ile, Gln, Glu,
```

```
        Tyr or Val
<220> FEATURE:
<221> NAME/KEY: VARIANT
<222> LOCATION: (24)...(24)
<223> OTHER INFORMATION: Xaa is Lys, Gln, Asn, His, Gly, Arg or Met
<220> FEATURE:
<221> NAME/KEY: VARIANT
<222> LOCATION: (25)...(25)
<223> OTHER INFORMATION: Xaa is any residue except Asn, Asp, Cys, His,
      Ile, Pro,
<223> Trp, Tyr or Val
<220> FEATURE:
<221> NAME/KEY: VARIANT
<222> LOCATION: (27)...(27)
<223> OTHER INFORMATION: Xaa is any residue except Cys, Gly, Phe, Pro,
      Ser or Trp
<220> FEATURE:
<221> NAME/KEY: VARIANT
<222> LOCATION: (28)...(28)
<223> OTHER INFORMATION: Xaa is any residue except Asp, Cys, His, Ile,
      Phe, Trp
<223> or Tyr
<220> FEATURE:
<221> NAME/KEY: VARIANT
<222> LOCATION: (29)...(29)
<223> OTHER INFORMATION: Xaa is Phe or Tyr
<220> FEATURE:
<221> NAME/KEY: VARIANT
<222> LOCATION: (30)...(30)
<223> OTHER INFORMATION: Xaa is any residue except Arg, Cys, Gly or Met
<220> FEATURE:
<221> NAME/KEY: VARIANT
<222> LOCATION: (31)...(31)
<223> OTHER INFORMATION: Xaa is Tyr, Trp, Phe or Asp
<220> FEATURE:
<221> NAME/KEY: VARIANT
<222> LOCATION: (32)...(32)
<223> OTHER INFORMATION: Xaa is Ser, Gly or Thr
<220> FEATURE:
<221> NAME/KEY: VARIANT
<222> LOCATION: (33)...(33)
<223> OTHER INFORMATION: Xaa is Gly or Ile
<220> FEATURE:
<221> NAME/KEY: VARIANT
<222> LOCATION: (35)...(35)
<223> OTHER INFORMATION: Xaa is Gly, Lys, Arg, Pro, Gln, Leu, Glu, Asn
      or Met
<220> FEATURE:
<221> NAME/KEY: VARIANT
<222> LOCATION: (36)...(36)
<223> OTHER INFORMATION: Xaa is Gly, Lys or Ala
<220> FEATURE:
<221> NAME/KEY: VARIANT
<222> LOCATION: (37)...(37)
<223> OTHER INFORMATION: Xaa is Asn, Lys or Ser
<220> FEATURE:
<221> NAME/KEY: VARIANT
<222> LOCATION: (38)...(38)
<223> OTHER INFORMATION: Xaa is any residue except Cys, His, Ile, Phe,
      Pro, Thr,
<223> Trp, Tyr or Val
<220> FEATURE:
<221> NAME/KEY: VARIANT
<222> LOCATION: (39)...(39)
<223> OTHER INFORMATION: Xaa is Asn or Tyr
<220> FEATURE:
<221> NAME/KEY: VARIANT
<222> LOCATION: (40)...(40)
<223> OTHER INFORMATION: Xaa is Arg, Asn, Lys, Gln or Val
<220> FEATURE:
<221> NAME/KEY: VARIANT
<222> LOCATION: (41)...(41)
<223> OTHER INFORMATION: Xaa is Phe, Tyr or Asp
<220> FEATURE:
<221> NAME/KEY: VARIANT
<222> LOCATION: (42)...(42)
<223> OTHER INFORMATION: Xaa is any residue except Cys, Gln, Gly, Phe
      or Trp
<220> FEATURE:
```

```
<221> NAME/KEY: VARIANT
<222> LOCATION: (43)...(43)
<223> OTHER INFORMATION: Xaa is Thr, Ser, Arg, Lys or Asp
<220> FEATURE:
<221> NAME/KEY: VARIANT
<222> LOCATION: (44)...(44)
<223> OTHER INFORMATION: Xaa is Ile, Leu, Trp, Arg, Lys, Thr, Glu, Ala,
      Gln or Val
<220> FEATURE:
<221> NAME/KEY: VARIANT
<222> LOCATION: (45)...(45)
<223> OTHER INFORMATION: Xaa is Glu, Asp, Ala, His, Met, Val, Gln, Lys,
      Arg or Pro
<220> FEATURE:
<221> NAME/KEY: VARIANT
<222> LOCATION: (46)...(46)
<223> OTHER INFORMATION: Xaa is Glu, Lys, Gln, Asp, Ala, Tyr or Ser
<220> FEATURE:
<221> NAME/KEY: VARIANT
<222> LOCATION: (48)...(48)
<223> OTHER INFORMATION: Xaa is any residue except Ala, Cys, Gly, Phe,
      Pro, Ser,
<223> Thr, Trp or Tyr
<220> FEATURE:
<221> NAME/KEY: VARIANT
<222> LOCATION: (49)...(49)
<223> OTHER INFORMATION: Xaa is any residue except Cys, Ile, Leu, Met,
      Phe, Pro,
<223> Ser, Tyr or Val
<220> FEATURE:
<221> NAME/KEY: VARIANT
<222> LOCATION: (50)...(50)
<223> OTHER INFORMATION: Xaa is Thr, Ala, Val, Ile, Phe, Leu, Met, Lys,
      Tyr or Arg

<400> SEQUENCE: 3

Cys Xaa Xaa Xaa Xaa Xaa Xaa Xaa Cys Xaa Xaa Xaa Xaa Xaa Xaa
 1               5                  10                  15

Xaa Xaa Xaa Xaa Xaa Xaa Xaa Xaa Cys Xaa Xaa Xaa Xaa Xaa Xaa
            20                  25                  30

Xaa Cys Xaa Xaa Xaa Xaa Xaa Xaa Xaa Xaa Xaa Xaa Xaa Cys Xaa
        35                  40                  45

Xaa Xaa Cys
    50

<210> SEQ ID NO 4
<211> LENGTH: 177
<212> TYPE: DNA
<213> ORGANISM: Artificial Sequence
<220> FEATURE:
<223> OTHER INFORMATION: Degenerate Sequence
<220> FEATURE:
<221> NAME/KEY: variation
<222> LOCATION: (1)...(177)
<223> OTHER INFORMATION: n is any nucleotide

<400> SEQUENCE: 4
ggnccnggng aygcntgygt nytnccngcn gtncarggnc cntgymgngg ntgggarccn      60
mgntgggcnt aywsnccnyt nytncarcar tgycayccnt tygtntaygg nggntgygar    120
ggnaayggna ayaayttyca ywsnmgngar wsntgygarg aygcntgycc ngtnccn       177

<210> SEQ ID NO 5
<211> LENGTH: 55
<212> TYPE: PRT
<213> ORGANISM: Homo sapiens

<400> SEQUENCE: 5

Thr Asp Ile Cys Lys Leu Pro Lys Asp Glu Gly Thr Cys Arg Asp Phe
 1               5                  10                  15
```

```
Ile Leu Lys Trp Tyr Tyr Asp Pro Asn Thr Lys Ser Cys Ala Arg Phe
            20                  25                  30
Trp Tyr Gly Gly Cys Gly Gly Asn Glu Asn Lys Phe Gly Ser Gln Lys
            35                  40                  45
Glu Cys Glu Lys Val Cys Ala
            50                  55

<210> SEQ ID NO 6
<211> LENGTH: 6
<212> TYPE: PRT
<213> ORGANISM: Artificial Sequence
<220> FEATURE:
<223> OTHER INFORMATION: Glu-Glu tag

<400> SEQUENCE: 6

Glu Tyr Met Pro Met Glu
 1               5

<210> SEQ ID NO 7
<211> LENGTH: 4
<212> TYPE: PRT
<213> ORGANISM: Artificial Sequence
<220> FEATURE:
<223> OTHER INFORMATION: Thrombin cleavage site

<400> SEQUENCE: 7

Leu Val Pro Arg
```